United States Patent [19]

van Staaveren

[11] Plant 4,600

[45] Oct. 7, 1980

[54] ALSTROEMERIA NAMED PINK TRIUMPH

[76] Inventor: M. C. van Staaveren, 30, Hornweg, 1432 GM Aalsmeer, Netherlands

[21] Appl. No.: 32,679

[22] Filed: Apr. 23, 1979

[51] Int. Cl.³ ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—Chas. W. Rummler

[57] ABSTRACT

A new alstroemeria cultivar characterized by the delicate pink and contrasting yellow coloration of its blossoms which have large outer petals of an overall pink color and smaller inner petals having a pink base color overlaid with yellow and lengthwise-extending streaks bearing rows of short, brown, pencil-stripe spots. This cultivar is also distinguished by its profuse production of flowers in a more-or-less continuous manner, fewer leaves than normal and improved autumn and winter flowering production.

1 Drawing Figure

BACKGROUND OF THE INVENTION

This new variety of alstroemeria originated as a seedling produced in the course of breeding efforts carried on by me at Aalsmeer, Holland, with the object of obtaining a wider color range and better autumn and winter flower production, this seedling resulting from my crossing of unpatented and unnamed breeding stock carried in my records as Ed 400 for the seed patent and 2171-1 as the pollen parent. Because of its interesting and novel coloring, this new plant was selected by me for propagation and trial and asexual propagation of this seedling plant was done by me at Aalsmeer, Holland. Subsequent propagation of this plant by root stock division through successive generations has shown that its new and novel characteristics hold true from generation to generation and appear to be firmly fixed.

DESCRIPTION OF THE DRAWING

My new variety of alstroemeria plant is illustrated by the accompanying full color photographic drawing which shows the form and color of the inflorescence, the colors shown being as nearly true as it is reasonably possible to be had with conventional photographic procedures.

DESCRIPTION OF THE NEW PLANT

The following is a detailed description of my new alstroemeria cultivar with color designations according to The R.H.S. Colour Chart published by The Royal Horticultural Society of London, England.

THE PLANT

Origin: Seedling.
Parentage:
*Seed parent.*—Breeding stock Ed 400.
*Pollen parent.*—Breeding stock 2171-1.
Classification:
*Botanic.*—Alstroemeria.
*Commercial.*—Hybrid alstroemeria.
Form: Tall and slender flower stalk with flower bearing branches in simple umbel arrangement at its top.
Height: Up to about 2 meters.
Growth: Sturdy and vigorous.

Branching: Each flower stalk bears 4 to 8 flower bearing branches at its top.
Foliage: Quantity — less than normal for alstroemeria plants.
*Number of leaves.*—20 to 30.
*Shape of leaf.*—Long and narrow.
*Texture.*—Soft.
*Color.*—Upper side — 146A. Under side — 191A.

THE BUD

Form: Pear shaped at the beginning and becoming long and pointed just before opening.
Opening rate: The bud opens slowly.
Peduncle:
*Length.*—Variable, growing outward from about 12 cm.

THE FLOWER

Blooming habit: Recurrent in spring and fall with more-or-less continuous and profuse production of flowers during each blooming period.
Flower size: Medium, depending upon season.
*Diameter.*—About 5 cm.
*Depth.*—About 4 cm.
Shape: Generally funnel-like.
Borne: Singly on a long peduncle.
Petalage: Number of petals — 6.
*Arrangement.*—Two concentric circles of 3 petals each.
*Form.*—Broad, elliptic and slightly serrated at the top.
*Color.*—Outer petals — Pink 55B to 37B. Inside petals — 55B-C overlaid with Yellow 13B. Reverse side — a little more pale than top side.
*Texture.*—Soft.
*Appearance.*—Shiny.
Persistence: The flowers hang on and dry.
Lasting quality:
*On the plant.*—About 10 days for each flower.
*As a cut flower.*—About 7 days for each flower.

REPRODUCTIVE ORGANS

Stamens:
*Arrangement.*—One opposite each petal.
*Anthers.*—Length — about 8 mm.
*Filaments.*—Length — about 4 cm.

Pistils: One.

*Length.*—About 3 cm.

This new plant merely resembles the alstroemeria variety "Regina" (U.S. Plant Pat. No. 3,284) differing particularly in that the new plant has flowers which, in general, are of a much deeper pink color than that of "Regina" and the nectar-bearing inner petals are of a much deeper yellow color than those of "Regina". Thus, in overall appearance, the inflorescence of this new plant is that of a pinkish-red color rather than the very light purple-pink of "Regina".

I claim:

1. A new and distinct alstroemeria cultivar substantially as herein shown and described, characterized by the distinctive overall red-pink coloring of the outer petals of its flowers and the sharply contrasting deep yellow coloring of its nectar-bearing inner petals, its abundant and substantially continuous production of flowers during each blooming season, and the long lasting quality of the individual blooms.

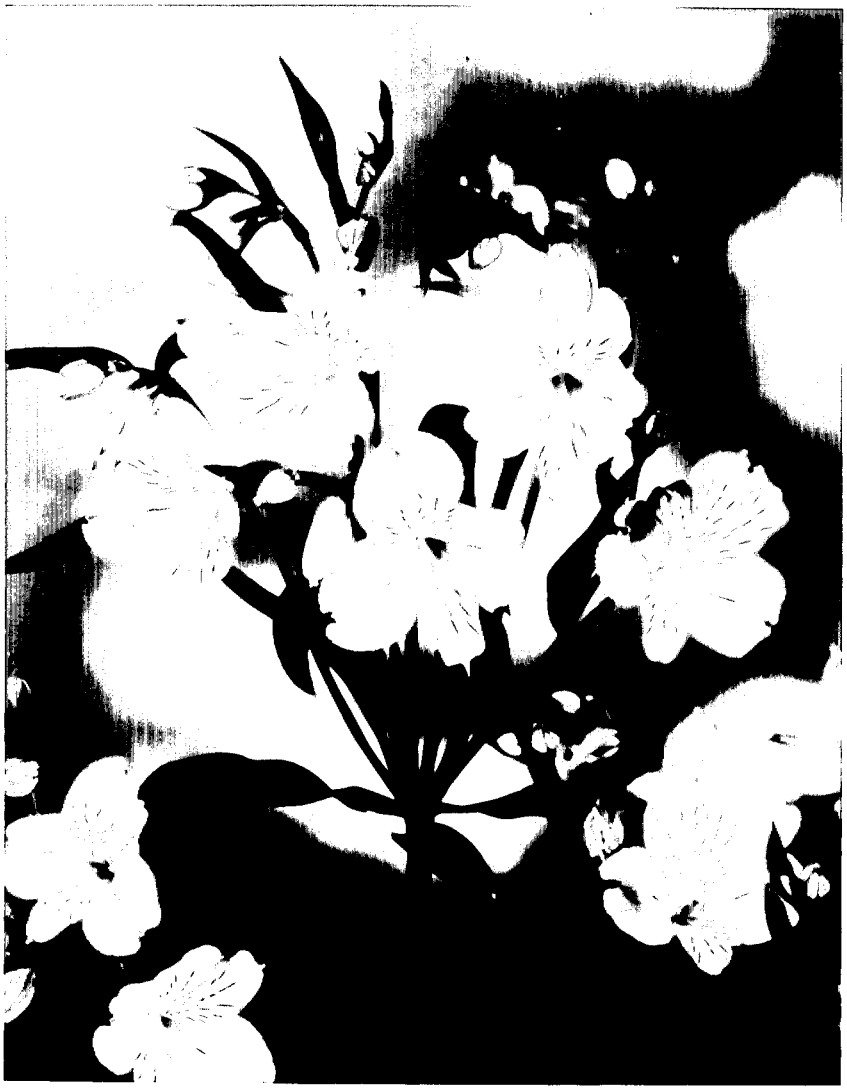

* * * * *